United States Patent [19]

Ohnishi

[11] Patent Number: 5,028,332
[45] Date of Patent: Jul. 2, 1991

[54] HYDROPHILIC MATERIAL AND METHOD OF MANUFACTURING

[75] Inventor: Makoto Ohnishi, Fuji, Japan

[73] Assignee: Terumo Kabushiki Kaisha, Tokyo, Japan

[21] Appl. No.: 383,067

[22] Filed: Jul. 21, 1989

[30] Foreign Application Priority Data

Jul. 22, 1988 [JP] Japan .................. 63-183095

[51] Int. Cl.$^5$ ............................. B01D 71/06
[52] U.S. Cl. .................. 210/500.34; 210/500.27; 210/500.35; 210/500.36; 210/500.38; 210/500.42; 210/506; 427/40; 427/41; 427/245; 428/304.4; 428/315.5
[58] Field of Search .................. 210/500.26, 500.36, 210/506, 490, 500.27, 500.35, 500.37, 500.38, 500.42, 500.33; 427/40, 41, 244, 245; 55/158; 428/304.4, 315.5

[56] References Cited

U.S. PATENT DOCUMENTS

| | | | |
|---|---|---|---|
| 3,666,693 | 5/1972 | Chapiro et al. | 210/500.27 |
| 4,032,440 | 6/1977 | Yasuda | 210/500.36 |
| 4,100,113 | 7/1978 | McCain | 428/333 |
| 4,280,970 | 7/1981 | Kesting | 210/654 |
| 4,346,142 | 8/1982 | Lazear | 427/44 |
| 4,413,074 | 11/1983 | Wrasidlo et al. | 210/490 |
| 4,432,875 | 2/1984 | Wrasidlo et al. | 210/500.34 |
| 4,594,079 | 6/1986 | Yamamoto et al. | 427/40 |
| 4,618,533 | 10/1986 | Steuck | 427/245 |
| 4,784,769 | 11/1988 | Giordano, Jr. et al. | 210/506 |
| 4,845,132 | 7/1989 | Masuoka et al. | 210/500.38 |

FOREIGN PATENT DOCUMENTS 0249513 7/1987 European Pat. Off. .

OTHER PUBLICATIONS

Journal of Membrane Science, vol. 39, No. 1, Oct. 1988, pp. 1–9.

Primary Examiner—W. Gary Jones
Attorney, Agent, or Firm—Burns, Doane, Swecker & Mathis

[57] ABSTRACT

A hydrophilic material having excellent hydrophilicity and fitness to living bodies and used for porous membranes or the like and also a method of manufacturing the same. The hydrophilic material is formed by subjecting at least part of the surfaces of a substrate of a polymer material to a plasma treatment to thereby produce a polymer radical and graft polymerizing therewith a block copolymer containing a hydrophilic monomer supplied in the gasious phase and a subsequently supplied hydrophobic monomer.

14 Claims, 2 Drawing Sheets

HYDROPHILIC MATERIAL AND METHOD OF MANUFACTURING

BACKGROUND OF THE INVENTION

This invention relates to a hydrophilic material having excellent hydrophilicity and fitness to living bodies and method of manufacturing the same and, more particularly, to a hydrophilic material, which may be used as gas exchange membranes for artificial lungs, ultrafilter or permeable membranes for artificial kidney, plasma separation membranes, blood component separation membranes and porous membranes to be held in contact in use with the liquid, blood and cells of such artificial internal organs as artificial livers and artificial pancreas, external circulation treatment devices and cell cultivation devices, and method of manufacturing the same.

In the prior art, various porous membranes for gas exchange, ultrafiltration and dialysis are used for the purposes of exchanging and removing matter in the fields of medical treatment, medicines, food industries, precision engineering industries and scientific experiments.

Where a porous membrane is used in an aqueous solvent such as an aqueous solution or blood, a hydrophilic porous membrane is used, or a hydrophobic porous membrane is used after being treated to impart the hydrophilicity. As the hydrophilic porous membrane, a porous membrane of a cellulose derivative, particularly cellulose acetate, is used.

As membranes prepared by imparting hydrophilicity to a hydrophobic porous membrane, Japanese Patent Disclosures 54-153872 and 61-42304 disclose membranes prepared by immersing a hydrophobic porous membrane substrate in an organic solvent of an a alcohol, followed by water substitution, and membranes prepared covering a hydrophobic polymer membrane with a surface active agent or a hydrophilic polymer material. Further, there have been proposed a method in which a hydrophobic porous membrane substrate is covered with a hydrophilic monomer and then subjected to a bridging treatment with an electron beam or gamma rays, and a method in which a hydrophilic plastic material is coupled by optical graft-polymerization, or plasma-initiated graft-polymerization as disclosed in Japanese Patent Disclosure 62-272705, to the membrane surface.

As porous membranes fitted to living bodies, more particularly used as such medical treatment material as in contact with living body component or cells, there have been developed hydrophobic porous membranes of polyethylene and polypropylene used as artificial lungs and plasma separators, hydrophilic membranes of cellulose-based and polyvinyl alcohol-based materials and membranes of such polymer materials as polymethylmethacrylate, polyacrylonitrile and polysulfone.

However, the hydrophilic porous membrane consisting of cellulose or cellulose derivatives is subject to swelling caused by water or like solvent in use. Therefore, when this porous membrane is assembled in an apparatus, the flow path of the apparatus is liable to be blocked with the swelling of the membrane. In such a case, the performance of the membrane cannot be sufficiently obtained. Further, in the case when a hydrophilic porous membrane consisting of a cellulose-based or polyvinyl alcohol-based material is used as medical treatment membrane in contact with blood, since it has the hydroxide group in the molecule, it renders a reinforcement system strongly active. Also, it induces leukopenia. In the method, in which the surfaces of a hydrophobic porous membrane are covered with a hydrophilic material, although it is simple, it is sometimes impossible to provide permanent hydrophilicity, or the cover material is liable to be dissolved or separated.

Further considering the fitness of the medical treatment porous membrane to blood, a membrane consisting of a hydrophobic polymer material such as polyethylene and polypropylene adsorbs greater amounts of plasma protein such as fibrinogen, although the activation of the reinforcement system is slight. Also, it is reported that a membrane, the surfaces of which are hydrophilic and have high water content, and to which less plasma protein and blood cell component are attached, is subject to extreme loss of platelets when it is held in contact with blood for a long time in or outside a living body.

Further, it is reported, for instance in the Journal of Biomedical Materials Research, Vol. 20, 919–927, 1986, that block copolymers present on the substrate surface in a status that it is in separate hydrophilic and hydrophobic phases shows excellent fitness to blood. Such block copolymers may be obtained by coating the substrate surfaces with a polymer material consisting of hydrophilic and hydrophobic macromolecule chains. With this method, however, it is difficult to cover even fine and highly hydrophobic inner pore surfaces of the polypropylene porous membrane uniformly with the block copolymer. Further, the block copolymer cover layer is liable to be separated and is weak in the mechanical strength.

SUMMARY OF THE INVENTION

The present invention has been intended in the light of the above problems, and its object is to provide a hydrophilic material, which is excellent in dimensional stability and fitness to living bodies, is free from separation of dissolved matter or cover layer and is excellent in safety, and a method of manufacturing the same.

To attain this object of the invention, there is provided a hydrophilic material, in which a block copolymer containing a material (X) having a hydrophilic polymer chain and a material (Y) having a hydrophobic polymer chain and/or these materials (X) and (Y) are coupled as graft chain to the surfaces of substrate (Z) of a polymer material.

Further, according to the invention there is provided a hydrophilic porous membrane, in which the substrate (Z) is a porous membrane, and the block copolymer and/or the materials (X) and (Y) are coupled as graft chain to at least part of the surfaces of the porous membrane substrate (Z) and inner pore surfaces thereof. The porous membrane as substrate (Z) is suitably composed of a hydrophobic polymer material with a threshold surface tension of 50 dyn/cm or below or with a water absorption factor of 1.0 % or below. Also, it is suitable that the bubble points is 0.5 to 20.0 kgf/cm$^2$, the thickness of the membrane is 20 to 300 μm, and the porosity is 20 to 80%. Further, the polymer material constituting the porous membrane is suitably a hydrophobic polymer material mainly composed of polypropylene.

Further, the hydrophilic material according to the invention is suitable as a material fitted to living bodies.

Further, according to the invention there is provided a method of manufacturing a hydrophilic material, which comprises a first step of subjecting at least part of the surfaces of a membrane substrate (Z) of a polymer material to a plasma treatment to thereby produce a polymer radical on the aforesaid surfaces, a second step of causing graft-polymerization with said polymer radical as point of start of polymerization by supplying a hydrophilic monomer (X) in gaseous phase to the substrate (Z) and a third step of causing graft-polymerization subsequent to the second step with the polymer radical present at the point of growth of the hydrophilic monomer (X) and/or radical on the surfaces of the substrate (Z) as point of start of polymerization by supplying a hydrophobic monomer (Y) in gaseous phase to the substrate (Z). According to the invention there is further provided a method of manufacturing a hydrophilic material, in which the second and third steps noted above are performed alternately in the mentioned order subsequent to the third step.

In the hydrophilic material according to the invention, the material (X) having the hydrophilic polymer chain and material (Y) having the hydrophobic polymer chain in the block copolymer are present in separate phases on the substrate surface, so that it provides excellent fitness (i.e., compatibility) to living bodies such as fitness to blood and resistance against diseases.

Further, with the porous membrane formed with the hydrophilic material according to the invention the block copolymer is chemically coupled as a graft chain to the porous membrane substrate, and therefore it is possible to produce a layer consisting of the separate hydrophilic and hydrophobic phases thinly and uniformly even on the inner pore surfaces of the porous membrane, which has hitherto been impossible with the prior art coating process. Thus, the membrane has fitness to living bodies and affinity to cells and is free from any separation phenomenon at the interface between the porous membrane substrate and block copolymer layer. Consequently, the block copolymer will never be dissolved in o separated into blood or a living body, and hence a highly safe membrane for medical treatment material can be provided. This membrane is useful as a plasma separation membrane, blood component separation membrane, membrane for gas exchange in artificial lungs, membrane for artificial kidney, membrane for artificial liver, membrane for artificial pancreas, various other membranes for external circulation treatment and also membranes for cell cultivation, bioreactor and DDS as well as carries of these membranes. Further, since the opposite ends of the polymer chain of the material (X) having the hydrophilic polymer chain are restricted by the hydrophobic polymer chains of the material (Y) having the hydrophobic polymer chain and by the polymer substrate (Z), the volume of discharge due to swelling by water absorption is reduced owing to the presence of the water-soluble polymer chain, compared to the hydrophilic porous membrane, in which a water-soluble polymer chain is coupled to inner pore surfaces, and correspondingly the volume and diameter of the inner pores are increased to promote such performance as permeation. Further, since the polymer substrate (Z) constituted by the porous membrane consists of a hydrophobic polymer material with a threshold surface tension of 50 dyn/cm or below or with a water absorption factor of 1.0% or below, the bubble point is 0.2 to 20.0 kgf/cm$^2$, the membrane thickness is 20 to 300 μm, and the porosity is 20 to 80%, the swelling of the membrane with moisture is eliminated to ensure excellent dimensional stability. Further, since the polymer, substrate (Z) is a hydrophobic polymer material mainly composed of polypropylene, a polymer radical capable of graft-polymerization can be readily formed, thus permitting ready control of the conditions for the synthesis in a status consisting of separate phases. Further, since the material fitted to living bodies according to the invention consists of the hydrophilic material, it has very excellent fitness to living bodies.

Further, since the method of manufacturing a hydrophilic material and a hydrophilic porous membrane therefrom according to the invention is one, in which a polymer radical is formed on the substrate surfaces by subjecting the substrate surfaces to a plasma treatment, it is possible to obtain efficient surface treatment. Further, the polymerization reaction is brought about by using neither polymerization initiator nor any catalyst, and also the graft chain is grown by supplying hydrophilic and hydrophobic polymer monomers in the gaseous phase. Thus, it is possible to obtain on the substrate a layer structure in a highly stable separated phase status.

DESCRIPTION OF THE PREFERRED EMBODIMENTS

Now, preferred embodiments of the invention will be described with reference to the drawings.

Figure 1:
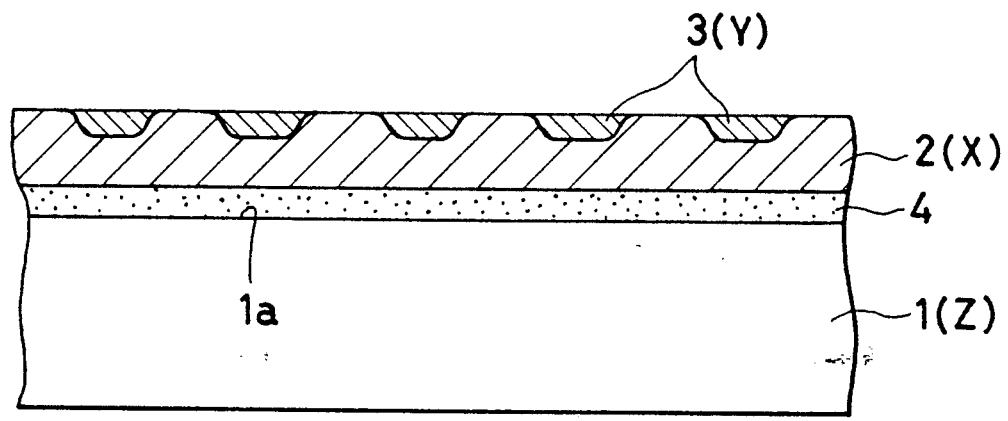
FIG. 1 is a schematic enlarged-scale sectional view showing the sectional structure of the hydrophilic material according to the invention.

FIG. 1 is a schematic sectional view showing an example of the hydrophilic material according to the invention. The illustrated hydrophilic material is obtained by coupling to the surfaces of a polymer membrane substrate (Z) a block copolymer containing a material (X) having a hydrophilic polymer chain and a material (Y) having a hydrophobic polymer chain as graft chain such that the materials (X) and (Y) are present in separate phases in a resultant layer. In the Figure, designated at 1 is the polymer-membrane substrate, 2 is the domain of the material (X) with the hydrophilic chain, 3 is the domain of the material (Y) with the hydrophobic chain, and 4 is an interface domain mainly composed of a graftomer between the polymer membrane substrate 1 and material (X) with the hydrophilic polymer chain.

In the porous membrane formed with the hydrophilic material according to the invention, the block copolymer containing the material (X) with the hydrophilic polymer chain and material (Y) with the hydrophilic polymer chain and/or the materials (X) and (Y) are coupled as graft chain to at least part of the membrane surfaces and inner pore surfaces of the porous membrane as the polymer substrate (Z) without utilizing any bridging reaction based on any bridging agent or light beam or radiations. The material (X) with the hydrophilic polymer chain is not particularly limited so long as it has a polymer chain having high affinity to, or solubility in water, but it suitably has a threshold surface tension of 50 dyn/cm or above or a water absorption factor of 1.0% or above. Examples of the material (X) are hydrophilic polymer materials based on acryl and methacryl derivatives such as polyhydroxyethylacrylate and polydimethylamino-methylmethacrylate, vinyl monomers containing polyether in the molecule such as polyethylene glycol and polypropylene glycol and hydrophilic polymer materials based on acrylamide and methacrylamide derivatives such as polyacrylamide, polydiacetoneamide and poly-N-methylacrylamide.

The material (Y) with the hydrophobic polymer chain is not particularly limited so long as its threshold surface tension or water absorption factor is less than that of the material (X) with the hydrophilic polymer chain. Examples of the material (Y) are polystyrene, polyethylmethacrylate, polybutylacrylate, polymethylmethacrylate, polyvinylidene chloride and polytetrafluoroethylene.

In the hydrophilic porous membrane according to the invention, the block copolymer or graft chain should be chemically coupled to and not be provided on coating or the like on the surfaces of the porous membrane substrate. Alternatively, it is possible that a hydrophilic polymer material is coupled to material surfaces by using such a bridging (i.e. cross-linking) agent as a multi-functional monomer or coupled to porous membrane substrate surfaces under such a polymerization condition that many bridge couplings are produced on the graft chain, e.g., grafting reaction or irradiation of the graft chain or monomer and/or polymer material as eventual graft chain with an electron beam, gamma rays, ultraviolet rays, etc. Further, by the term "hydrophilic porous membrane" according to the invention is meant a membrane having surfaces which are more hydrophilic, i.e., with higher free energy than with the polymer substrate (Z).

The hydrophilic porous membrane according to the invention has a graft chain having a basic structure with hydrophobic (Z), hydrophilic (X) and hydrophobic (Y) phases in the mentioned order. The membrane according to the invention is obtained by causing growth of the graft chain by causing contact of a monomer in gaseous phase with the polymer substrate (Z). Basically, it has a graft chain consisting of a block copolymer with hydrophilic (X) and hydrohobic (Y) phases. However, the invention also covers a structure, the graft chain of which is constituted by a block copolymer with the hydrophilic (X) and hydrophobic (Y) phases coupled alternately, for instance in the order of (X)—(Y)—(X) or (X)—(Y)—(X)—(Y). Further, a structure is covered, in which hydrophilic (X) and hydrophobic (Y) graft chains are coupled in a mixed state to the substrate surfaces.

Further, with the hydrophilic porous membrane according to the invention a hydrophobic polymer material constituting the porous membrane as polymer substrate has a threshold surface tension of 50 dyn/cm or below or a water absorption factor of 1.0%. Also, it is preferred that the bubble point is 0.2 to 20.0 kgf/cm$^2$, the membrane thickness is 20 to 300 $\mu$m, and the porosity is 20 to 80%. The bubble point means a value obtained by a measurement conducted by a method prescribed in ASTM F-316 and with isopropyl alcohol (IPA) as solvent. The porosity means a percentage value of the ratio of the volume of the pores to the overall volume of the membrane.

The polymer substrate (Z) preferably consists of a hydrophobic polymer material mainly composed of polypropylene.

The hydrophilic material according to the invention can be obtained by producing a polymer radical on the surfaces of the polymer substrate (Z) by subjecting the substrate to a low temperature plasma treatment, then causing graft polymerization on the substrate surfaces by supplying the hydrophilic monomer (X) in gaseous phase to the substrate surfaces under a reduced pressure of 0.1 to $10^2$ mm Hg and with the polymer radical as the point of initiation of the polymerization, removing most of non-reacted hydrophilic monomer (X) by pressure reduction and then causing graft polymerization by supplying the hydrophobic monomer (Y) in gaseous phase under a reduced pressure of 0.1 to $10^2$ torr and with the polymer radical present at point of growth of the hydrophilic polymer chain (X) and/or polymer radical on the surfaces of the substrate (Z) as point of initiation of the polymerization.

The hydrophilic and hydrophobic monomers (X) and (Y) should be capable of radical polymerization. Examples of the hydrophilic monomer (X) are 2-hydroxyethyl-methacrylate, N-vinylpyrrolidone methacrylate, N-methylacrylamide, N,N-dimethylacrylamide and dimethylamino-ethylmethacrylate. Examples of the hydrophobic monomer (Y) are acrylate- and methacrylate-based monomers such as methylmethacrylate, ethylmethacrylate, butylacrylate, styrene, ethylene tetrafluoride and perfluoromethacrylate and also derivatives of acrylamide and methacrylamide.

The hydrophilic porous membrane according to the invention can be obtained by applying the method of manufacturing the hydrophilic material to the surfaces of the porous membrane as polymer substrate (Z).

The hydrophilic porous membrane obtained in this way has the block copolymer with the hydrophobic and hydrophilic chains as graft chain on the membrane surfaces, and the formation of a layer, in which separate hydrophilic and hydrophobic phases are present in a mixed state, permits high fitness to blood and to living bodies to be obtained. The cell surface of living body has hydrophilic and hydrophobic portions in a mixed state. Therefore, the fitness of the surface of medical treatment tools is increased with a structure, in which two different kinds of portions are present in a mixed state. With the sole hydrophobic portion the viscosity with respect to globulin or like protein is undesirably high. On the other hand, with the sole hydrophilic portion the viscosity is too low.

Further, since the hydrophilic porous membane noted above is free from any bridging reaction with a bridging agent or radiation, the polymer chain obtained by the graft polymerization has a stable structure energy-wise. If necessary, the phase separations status of the block copolymer can be controlled by treating the membrane surfaces with a good solvent for the graft chain. Further, the above hydrophilic porous membrane permits variation of the degree of the hydrophilicity or hydrophobicity or control of the status of gathering of chains to be obtained by appropriately selecting the molecular weights of the materials (X) and (Y) with the respective hydrophilic and hydrophobic chains on the surfaces. Such control of the phase separation status cannot be obtained with blendomer. Therefore, the surfaces of the hydrophilic porous membrane according to the invention has satisfactory fitness to living bodies which cannot be seen with an homopolymer or random copolymer.

Further, since the block copolymer is chemically coupled as a graft chain to the porous membrane, unlike the prior art coating process, there is no possibility of separation at the interface between the substrate and block copolymer layer. As a result, there is no possibility of dissolution or separation of the block copolymer in or into blood or living body, and it is possible to provide a highly safe membrane. Further, since the membrane is obtained by coupling the graft chain to the substrate surfaces by supplying a monomer in the gaseous phase, it is possible to obtain a thin surface domain in a uniform phase separation status. Thus, the hydrophilic porous membrane according to the invention is applicable to catheters of various shapes, medicals, artificial organs such as artificial bones and veins, artificial internal organs, prolonged released medical treatment articles, etc. which have hitherto been considered to be difficultly covered. Further, since the polymer substrate (Z) of the membrane consists of a hydrophobic polymer material, the membrane is free from swelling by absorbing water and has excellent dimensional stability. Further, it has fitness to living bodies owing to three-dimensional block copolymer having hydrophobic (Z), hydrophilic (X) and hydrophobic (Z) phases in the mentioned order.

With the hydrophilic porous membrane according to the invention, since the opposite ends of the hydrophilic polymer chain are restricted by the hydrophobic polymer chains, the displacement volume is reduced compared to the hydrophilic porous membrane, in which a hydrophilic polymer chain is merely graft polymerized, and the pore volume and pore diameter of the membrane are correspondingly increased, thus providing for high water permeability. Further, where the porous substrate consists of a polymer material having three carbon atoms in the molecule like polypropylene, the monomer produces a polymer radical, thus permitting ready control of the conditions of synthesis of a hydrophilic porous membrane having a surface in a status with separate phases.

Further, in order to improve the fitness of the hydrophilic porous membrane according to the invention to living bodies and blood or provide a certain specific function such as selective adsorbing property, simulative response, catalytic activity and prolonged release, physiological materials or functional polymer materials may be coupled to the hydrophilic or hydrophobic polymer chain. In this case, the hydrophilic porous membrane according to the invention can be an excellent membrane.

Further, since in the method of manufacturing a hydrophilic porous membrane according to the invention a polymer radical is produced on the surfaces of the polymer substrate (Z) by subjecting the substrate to a low temperature plasma treatment, unlike the case of a treatment with gamma rays or like highly permeable radiation, there is less influence on the bulk, and it is possible to obtain effective surface treatment. Further, since the method is a synthesis method of a clean and dry process of causing growth of a graft chain containing the material (X) having a hydrophilic polymer chain and material (Y) having a hydrophobic polymer chain without use of any polymerization initiator or catalyst for the polymerization reaction but by supplying a monomer in the gaseous phase, it is possible to obtain a highly safe hydrophilic porous membrane. Further, since no solvent is used, such effect as chain transfer gel effect is difficult to produce, and a membrane having a desired status of phase separation can be synthesized efficiently.

EXAMPLES

Examples 1 to 3 and Comparative Example 1

A porous membrane consisting of polypropylene and with a length of 230 mm, a width of 130 mm a thickness of 130 $\mu$m and a pore diameter of 0.6 $\mu$m was used as a substrate and subjected to a low temperature plasma treatment under conditions of an argon pressure of 0.1 torr, 80 W and 20 sec. Then, the pressure was reduced to 0.01 torr or below, and then graft polymerization was caused to proceed in gaseous phase for 3 minutes by supplying N,N-dimethylacrylamide (hereinafter referred to as DMAA) as hydrophilic monomer under a pressure of 0.8 torr. Thereafter, non-reacted DMAA was removed by pressure reduction for 5 minutes, and then a graft chain of n-butylacrylate (hereinafter referred to as BA) was grown by supplying BA as a hydrophobic monomer under a pressure of 8 torr and at 25° C. to the surfaces, to which poly-DMAA had been coupled by graft polymerization. In Examples 1 to 3, the time of graft polymerization of BA was set to be 30 seconds, one minute and two minutes, respectively, thus synthesizing respectively three different hydrophilic porous membranes having surfaces with different poly-BA chain lengths.

In Comparative Example 1, graft polymerization was performed by supplying the sole DMAA, and no graft polymerization with n-BA was performed.

The hydrophilic porous membranes having block copolymer of poly-DMAA and poly-BA as graft chain were then washed with methanol and dimethylformamide and subjected to extractive substances test, hemolytic toxicity text, acute toxicity text, intracutaneous reaction test, heat generation test and transplantation test conforming to the solution administration plastic vessel standards of the PHARMACOPOEIA of Japan. They all passed these tests.

Figure 2:
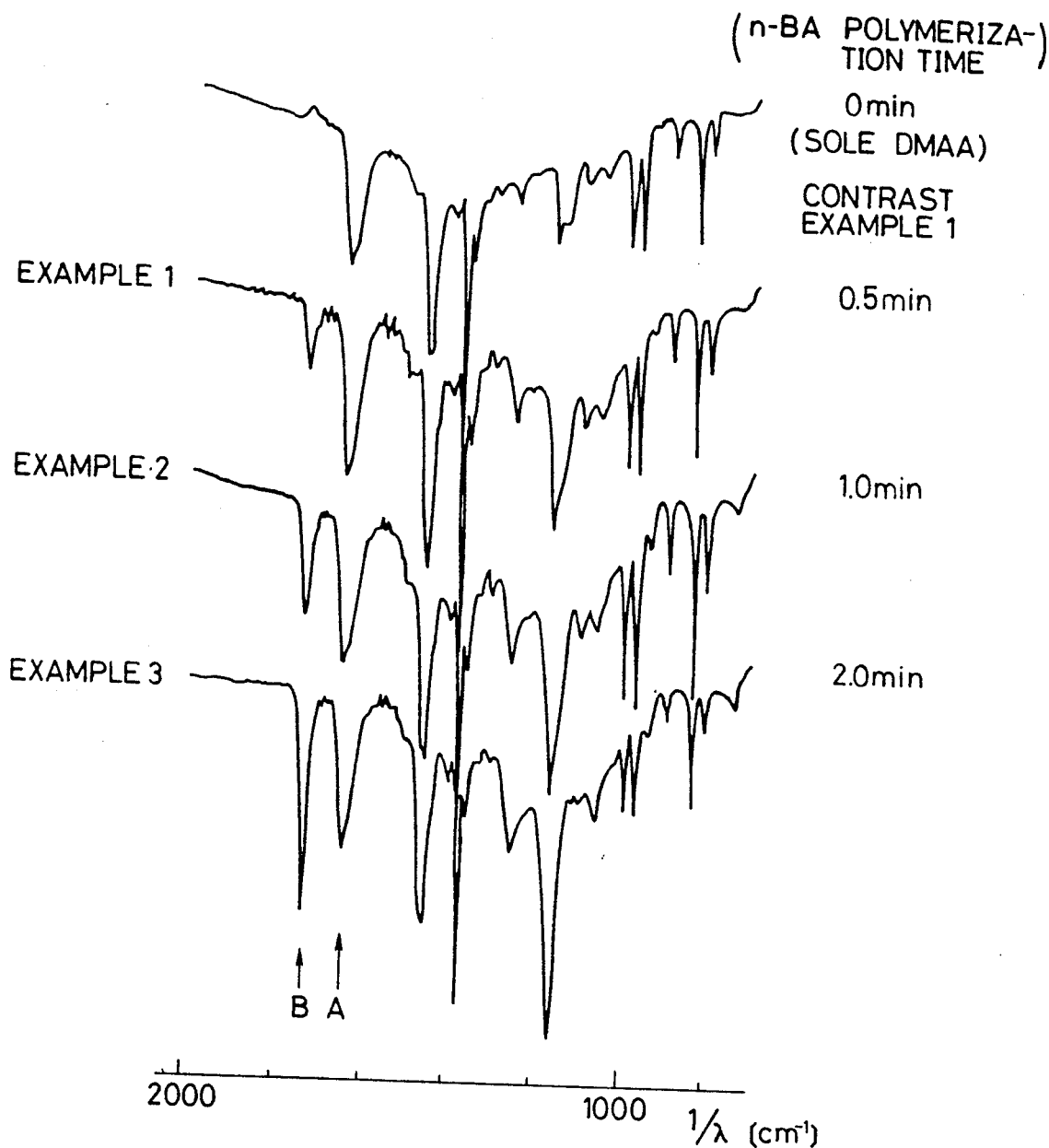
FIG. 2 is a spectral diagram showing infrared absorption spectra of various experimental examples of porous membrane as the hydrophilic material according to the invention and contract examples.

FIG. 2 shows results of surface analysis of the surface layer portion of the hydrophilic porous membranes in Examples 1 to 3 using an infrared absorption spectrum FT-IR-ATR ("Model FTS 40" manufactured by Japan Biorad Co., Ltd.). Labeled A is absorption of poly-DMAA coming from

and B absorption of poly-BA coming from

With increase of the time of reaction with BA the absorption B becomes stronger compared to the absorption A, indicating the increase of the proportion of poly-BA.

Table 1 shows results of analysis of the surface of the hydrophilic porous membranes in Examples 1 to 3 with a scanning type electron microscope (ESCA, "Model JSM-840" by Nippon Denshi). It was observed that the amount of nitrogen on the surface due to poly-DMAA reduced with increasing time of reaction with BA.

From the above, it was found that the hydrophilic porous membrane according to the invention has both hydrophilic and hydrophobic polymer chains on the membrane surface and is capable of control of the structure of the microscopic status of phase separation in a wide range with selection of conditions of reaction.

Then, platelet adhesion test was conducted on the hydrophilic porous membranes according to the invention to examine the fitness (i.e. compatibility) of the membranes to living bodies. A solution containing 3.8% of sodium citrate was held in contact with platelet rich plasma (PRP) extracted from fresh human blood added by the same volume at room temperature for 30 minutes. Then, the resultant system was washed with physiologic salt water and fixed with a solution containing 2.5% of glutaraldehyde. The resultant system was observed with an electron microscope (ESCA "Model JSM-840" by Nippon Denshi). It was found that substantially no platelets were attached to the surfaces of the porous membrane according to the invention and that very slight platelets attached were not substantially deformed. It was thus made clear that the surfaces of the porous membrane have high affinity to cells and living body components.

Table 1 lists the bubble point, water permeation and plasma separation of the hydrophilic porous membrane according to the invention. The plasma separation was obtained with cow blood by using a $24-cm^2$ minimojule and at a creep speed of 30 $sec^{-1}$. The hydrophilic porous membrane according to the invention has excellent performance as plasma separation membrane as well.

Comparative Example 2

As in Examples 1 to 3, a platelet adhesion test was conducted on a non-treated polypropylene porous membrane. It was found that many deformed platelets attached to the membrane surfaces, covering about 30% of the surfaces.

Example 4

A porous membrane was synthesized by using DMAA as a hydrophilic monomer and styrene as a hydrophobic monomer in the same method as in Example 1 except for that the conditions for the graft polymerization were changed, and it was evaluated. The obtained porous membrane was found to have excellent fitness to living bodies as in Example 1. This porous membrane was given a bending stress and, in this state, was observed with an electron microscope to observe no particular change.

Comparative Example 3

Coating of a block copolymer consisting of DMAA and styrene on the surfaces of a polypropylene porous membrane used as a substrate in Example 4 was tried, but it was impossible to obtain a thin and uniform coating. Further, the membrane was given a bending stress as in Example 4 and in this state was observed with an electron microscope. Cracks and a surface separation phenomenon were observed where the block copolymer was coated.

Examples 5 to 8, Comparative Example 4

Experiments were conducted on the reduction of extractive substances, found in the porous membrane according to the invention. Table 2 shows the result. The synthesis was performed under the same conditions as in Examples 1 to 3 except for that n-BA was replaced with EA (ethylacrylate) and that the polymerization time was set differently in Examples 5 to 8. In Comparative Example 4 no EA polymerization was performed.

As for the measurement of the extractive substances, to about 1 g of membrane 100 times of distilled water was added for autoclave extraction at 115° C. for 30 minutes. Then, UV in a range of 350 to 220 nm was measured to obtain the maximum value (delta UV) of the light absorbance. With these membranes, the maximum value (delta UV) was at 220 nm.

The extractive substances were analyzed by liquid chromatography. The main component was poly-DMAA, which was reduced in Example 8 to about one-eighth compared to Comparative Example 4.

TABLE 1

| | Polymerization Time [min] | | Bubble Point | Water Permeation | Plasma Separation | ESCA | |
|---|---|---|---|---|---|---|---|
| | DMAA | n-BA | [Kgf/cm²] | [ml/min · m² · mmHg] | [ml/min · cm² · mmHg] | N/C | O/C |
| Example 1 | 3 | 0.5 | 1.03 | 126 | 0.32 | 0.065 | 0.133 |
| Example 2 | 3 | 1.0 | 1.05 | 132 | 0.33 | 0.052 | 0.177 |
| Example 3 | 3 | 2.0 | 1.08 | 118 | 0.29 | 0.037 | 0.222 |
| Comparative Example 1 | 3 | 0 | 0.97 | 82 | 0.28 | 0.093 | 0.261 |

TABLE 2

| | Polymerization Time [min] | | Water Permeation [ml/min · m² · mmHg] | Extractive Substances ΔUV |
|---|---|---|---|---|
| | DMAA | EA | | |
| Example 5 | 3 | 0.5 | 145 | 0.052 |
| Example 6 | 3 | 1.0 | 170 | 0.036 |
| Example 7 | 3 | 2.0 | 192 | 0.012 |
| Example 8 | 3 | 4.0 | 166 | 0.011 |
| Comparative Example 4 | 3 | 0 | 102 | 0.082 |

What is claimed is:

1. A hydrophilic material comprising a block copolymer containing a material (X) having a hydrophilic polymer chain and a material (Y) having a hydrophobic polymer chain, the copolymer being coupled as a substantially non-crosslinked graft chain to the surface of a substrate (Z) of a polymer material.

2. A material compatible with a living body comprising the hydrophilic material according to claim 1.

3. A hydrophilic porous membrane, comprising:
   (a) a porous membrane substrate (Z);
   (b) a hydrophilic polymer chain (X) grafted to at least a portion of the substrate (Z); and
   (c) hydrophobic polymer chain (Y) grafted to the polymer chain (X);
   wherein the polymer (X) and polymer (Y) together comprise a substantially non-crosslinked block copolymer, and wherein said copolymer is grafted to at least a portion of the surface of the substrate (Z)

and to at least a portion of the inner pore surfaces of the substrate (Z).

4. The hydrophilic porous membrane according to claim 3, wherein said substrate (Z) comprises a hydrophobic polymer material having at least one of a threshold surface tension of 50 dyne/cm or below or a water absorption factor of 1.0% or below, and wherein said porous membrane has a bubble point of from about 0.2 to about 20.0 kgf/cm$^2$, a membrane thickness of from about 20 to about 300 μm and a porosity of from about 20 to about 80 percent.

5. The hydrophilic porous membrane according to claim 3 or 4, wherein said substrate (Z) comprises a hydrophobic polymer material including polypropylene.

6. The hydrophilic porous membrane according to claim 3, wherein polymer (X) comprises repeating units of an acryl or methacryl derivative, a vinyl monomer containing a polyether group, or an acrylamide or methacrylamide derivative.

7. The hydrophilic porous membrane according to claim 6, wherein polymer (X) comprises repeating units selected from the group consisting of polyhydroxyethylacrylate, polydimethylamino-methylmethacrylate, polyethylene glycol, polypropylene glycol, polyacrylamide, polydiacetoneamide, poly-N-methylacrylamide, and combinations thereof.

8. The hydrophilic porous membrane according to claim 3, wherein polymer (Y) comprises a polymer having a threshold surface tension or water absorption factor less than that of polymer (X).

9. The hydrophilic porous membrane according to claim 3, wherein polymer (Y) comprises repeating units selected from the group consisting of polystyrene, polyethylmethacrylate, polybutylacrylate, polymethylmethacrylate, polyvinylidene chloride, polytetrafluoroethylene and combinations thereof.

10. The hydrophilic porous membrane according to claim 3, wherein water permeability through said porous membrane is substantially maintained when said porous membrane is in contact with an aqueous medium.

11. A method for producing a hydrophilic material, comprising the steps of:
 (a) plasma treating at least part of the surface of a polymer substrate (Z), thereby producing polymer radicals on the surface of substrate (Z);
 (b) graft polymerizing a gaseous hydrophilic monomer (X) onto the polymer substrate surface via said polymer radicals, thereby forming a polymer (X) attached at one end to said surface; and
 (c) graft polymerizing a gaseous hydrophobic monomer (Y) onto said hydrophilic polymer (X) at a point of growth of the hydrophilic polymer (X), thereby forming a polymer (Y) attached at one end to said polymer (X), the polymers (X) and (Y) forming a substantially non-crosslinked copolymer.

12. The method according to claim 11, including after step (c), the step of (d) graft polymerizing monomer (X) onto polymer (Y) at the point of growth of polymer (Y), thereby forming a copolymer (X)—(Y)—(X).

13. The method according to claim 12, including after step (d), repeating at least once steps (c) and (d), thereby producing a graft copolymer on substrate (Z) which includes alternating blocks of polymer (X) and polymer (Y).

14. The method according to claim 11, 12 or 13, wherein the substrate (Z) is porous, and wherein the graft polymerization of monomer (X) and monomer (Y) takes place at the inner pore surfaces of polymer (Z).

* * * * *